United States Patent [19]
Humbert et al.

[11] Patent Number: 5,230,700
[45] Date of Patent: Jul. 27, 1993

[54] ORTHOPEDIC APPARATUS FOR PERSONS HANDICAPPED IN ONE LEG

[76] Inventors: Charles Humbert, Pont 8, Le Locle, Switzerland, 2400; Peter Jenoure, Bielstrasse 58, Oberwil, Switzerland, 4140

[21] Appl. No.: 613,787
[22] PCT Filed: Apr. 26, 1990
[86] PCT No.: PCT/CH90/00113
 § 371 Date: Dec. 20, 1990
 § 102(e) Date: Dec. 20, 1990
[87] PCT Pub. No.: WO90/13273
 PCT Pub. Date: Nov. 15, 1990

[30] Foreign Application Priority Data
Apr. 28, 1989 [CH] Switzerland .......................... 1623/89
Feb. 5, 1990 [CH] Switzerland ............................ 351/90

[51] Int. Cl.⁵ .............................................. A01F 5/00
[52] U.S. Cl. ......................................... 602/23; 135/65; 602/5
[58] Field of Search ............... 602/4, 5, 23, 25, 26-29; 135/65, 66, 68

[56] References Cited

U.S. PATENT DOCUMENTS

| D. 226,203 | 1/1973 | Gibbs et al. | 273/162 R |
|---|---|---|---|
| 1,066,190 | 7/1913 | Ellingsworth | 602/5 |
| 1,336,695 | 4/1920 | Gromes . | |
| 1,660,721 | 2/1928 | Schrag | 602/23 X |
| 2,543,847 | 3/1951 | Hallstedt | 602/4 |
| 4,483,336 | 11/1984 | Deiteh | 602/4 |
| 4,522,199 | 6/1985 | Waddell et al. | 602/23 |
| 4,608,971 | 9/1986 | Borschneck | 602/73 |
| 4,641,882 | 2/1987 | Young . | |
| 4,967,734 | 11/1990 | Rennex | 602/23 |

FOREIGN PATENT DOCUMENTS 488296 9/1918 France .
8400898 3/1984 World Int. Prop. O. .

OTHER PUBLICATIONS

"Gim—me Putter" advertisement, 1966.
"Die Mainzer-Huftentlastungs-Orthesebiem M. Perthes," *Medizinisch-Orthopadische Technik*, vol. 103, No. 2, Mar./Apr. 1983, pp. 45-48.

Primary Examiner—Richard J. Apley
Assistant Examiner—Linda C. M. Dvorak
Attorney, Agent, or Firm—Pennie & Edmonds

[57] ABSTRACT

An orthopedic apparatus for persons handicapped in one leg. The apparatus includes a rigid member one end of which engages the ground between the legs of the user and the other end of which includes a saddle for engaging the individual between his legs in the crotch area.

7 Claims, 3 Drawing Sheets

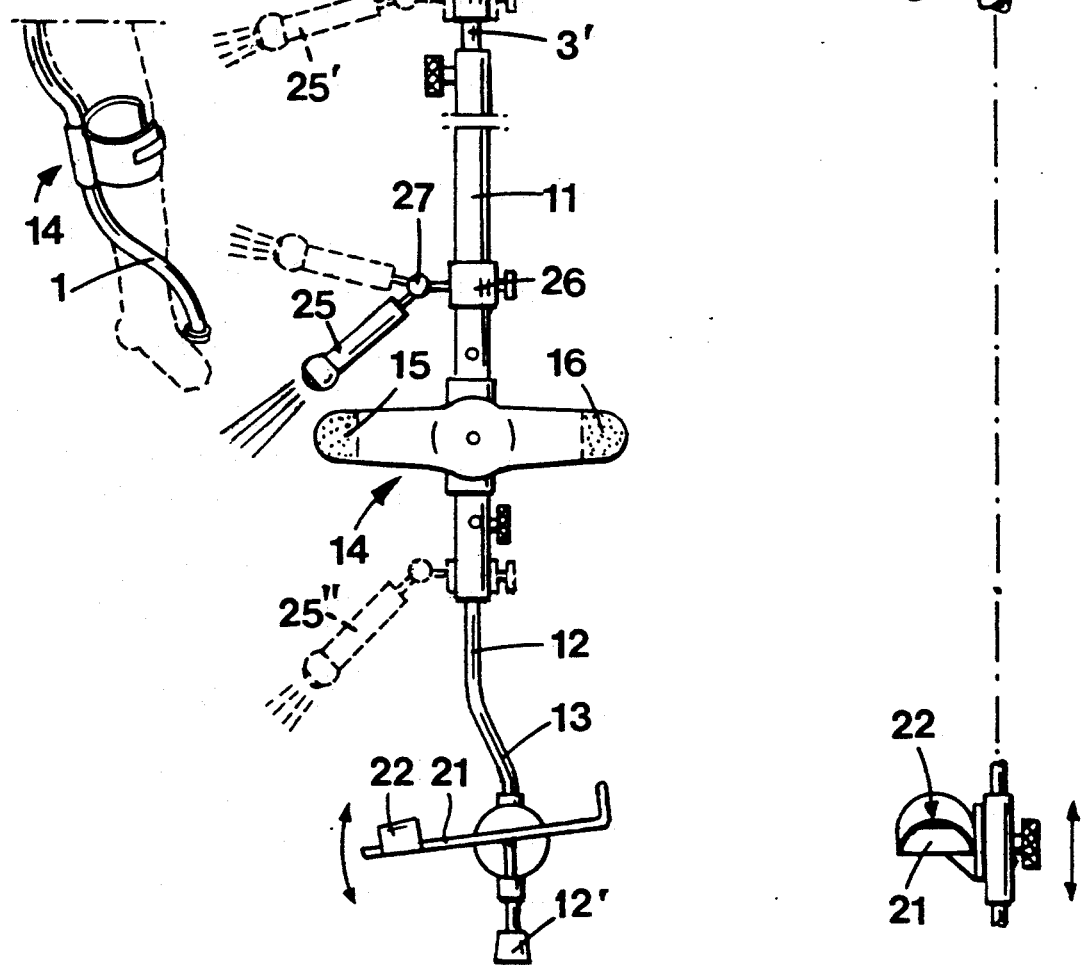

ORTHOPEDIC APPARATUS FOR PERSONS HANDICAPPED IN ONE LEG

BACKGROUND OF THE INVENTION

1. Technical Field

The present invention relates to an orthopedic apparatus for persons handicapped in one leg, which includes a support member that relieves the weight of the body from that leg both when the user is in motion and not, without exerting any force on the thigh muscles and while leaving the user's hands and arms totally free.

2. Background Art

Numerous devices are known for helping a person handicapped in one leg to walk. After the cane and the crutch held under the armpit, the use of the so-called "English" cane has spread considerably. This English cane includes a segment which lies parallel to the forearm and supports the elbow by a cup, while the hand grips a handle. In use, a number of drawbacks have appeared, such as for example : the transmission of the weight through the arms and the elbow, and the need to grip the canes firmly with the hands, which puts a considerable strain on these body parts, causes excessive fatigue and can even provoke distal or proximal articular inflammations of the upper limbs.

The present invention is aimed at providing an orthopedic apparatus for persons handicapped in one leg (post-traumatic or postoperative period requiring total or partial relieving of the limb), which is constructed in such a manner as to avoid the above-mentioned side effects and to facilitate complete rehabilitation.

For this purpose, an apparatus was proposed [R. Volkert and Dr. Steeger, 4520 Medizinisch-Orthopädische Technik, vol. 103 (1983) No 2, March-April, p. 45-48], which was designed for relieving the handicapped leg and for allowing the user to walk without the help of his hands or of any other orthopedic means. The apparatus which was proposed embraces the thigh and supports the dorsal part of the pelvis. As a result, the thigh muscles are strongly compressed and they transmit the weight of the body to a metallic member, the lower end of which is constructed to lean against the ground, both when walking and when standing.

However, to wear such an apparatus is bound to be relatively rapidly painful to the thigh.

An orthopedic apparatus was also proposed (U.S. Pat. No. 4,641,882) for the same purpose, comprising a member for leaning against the ground, which is rigid and of an elongated shape, and which is provided at its upper end with a saddle designed for receiving the user in a seated position, as when sitting on a bicycle. Two handles are integral with this saddle for the user to hold with his hands as he walks, so as to maintain the saddle in contact with his buttocks. The saddle relieves the handicapped leg of the weight of the body only when the user stops and not when he walks.

SUMMARY OF THE INVENTION

The present invention is aimed at providing an orthopedic apparatus for persons handicapped in one leg, which relieves the handicapped leg of the weight of the body both when the user walks and when he stops, without any force being exerted on the thigh muscles for transmitting the weight to a member leaning against the ground, and which leaves the user's hands and arms totally free.

The apparatus of the invention is specifically directed to an orthopedic apparatus for persons handicapped in one leg which is sometimes referred to as a "sitting stick". This apparatus comprises a rigid member (1) having upper and lower portions, first and second ends and an elongated shape, the first end associated with the upper portion and including a saddle (2) for supporting the user's weight, the second end associated with the lower end (12') and including means for leaning against the ground. The saddle (2) has a front portion, a central portion, a back portion and two side portions, wherein the front and back portions are raised with respect to the central portion and the central portion is higher than the side portions to provide a useful surface area which is configured and dimensioned to be engaged between the user's legs. The rigid member (1) is attached to one of the side portions of the saddle and is provided with at least one device (4) for attachment to the handicapped leg, which device is operatively associated with the saddle and the rigid member for placing the upper portion (3,3') of the rigid member against the inside of the thigh of the handicapped leg while maintaining the useful surface area of the saddle offset with respect to the longitudinal medial plane (28) of the user's body and facing the ischium (29) which is adjacent the handicapped leg. This attachment device (4) includes means for allowing the rigid member (1) to follow any swinging movement of the handicapped leg imparted by the user when his other leg supports the whole weight of the user's body, thus making it possible to for the user to walk with his hands and arms free and without help form other orthopedic means. Also, the lower end of the rigid member is provided with a plantar support (21), the height and inclination of which can be adjusted, and which is provided with attachment means (22) for forming a stirrup that enables the user to lift the apparatus when lifting the handicapped leg.

BRIEF DESCRIPTION OF THE DRAWINGS

The appended drawings illustrate, by way of examples, two embodiments of the invention and another version of the same.

FIG. 3 is a side view of the second embodiment;

FIG. 4 is a cross-section of the upper part of the second embodiment, taken as indicated by the arrow 4 of FIG. 3;

FIG. 5 is a perspective view of the lower part of said version;

The corresponding parts of the different embodiments are designated by the same reference numerals.

DETAILED DESCRIPTION OF THE INVENTION

Figure 1:
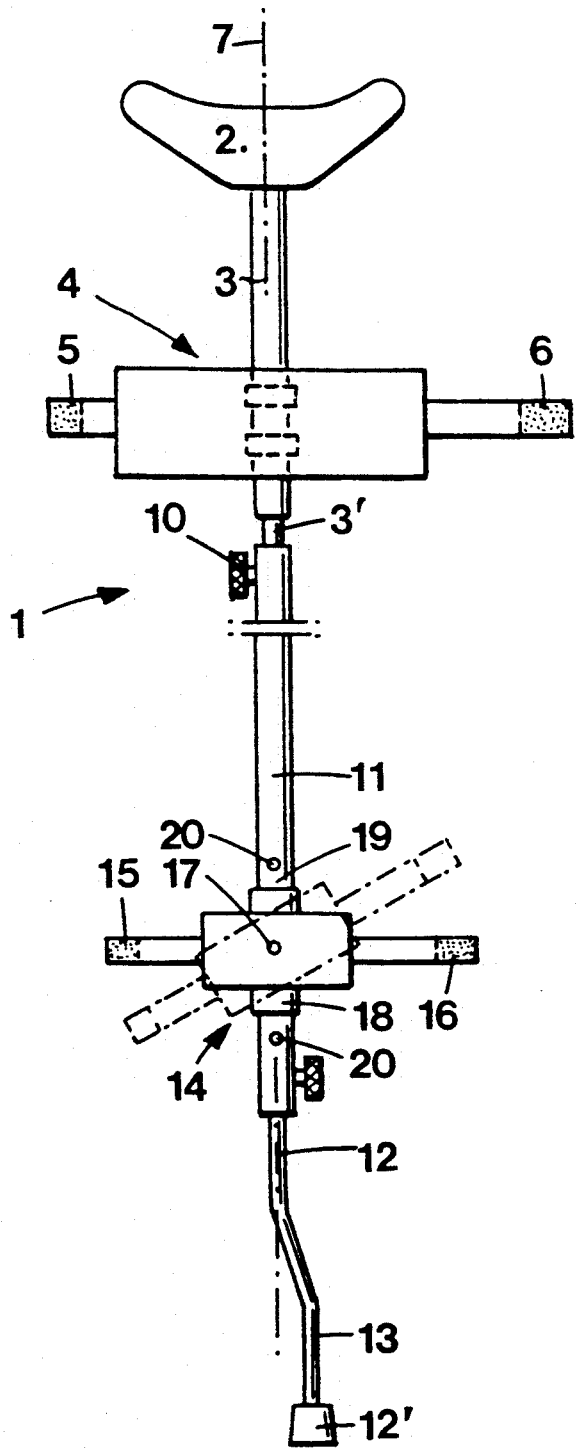
FIG. 1 is a side view of the first embodiment.
Figure 2:
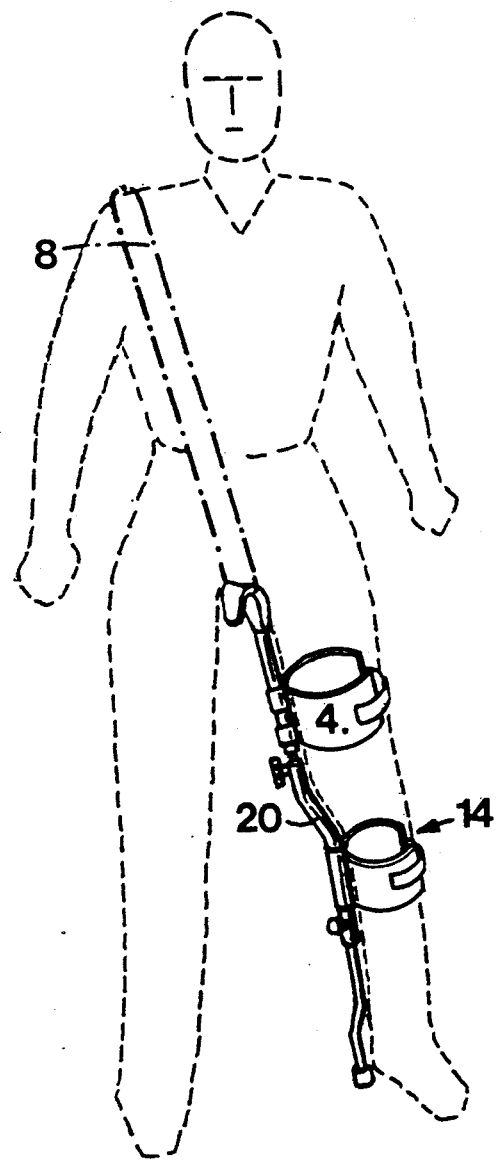
FIG. 2 is a perspective view of this embodiment, worn by a man.

In FIG. 1, a member is shown at reference 1 for leaning against the ground, which is rigid and of an elongated shape; its length is adjustable. This member 1 is provided at its upper part with a saddle 2 having the actual shape of a saddle in the mathematical sense of the word, i.e. when viewed in one axial cross-section, the centre of the saddle is the lowest point and when viewed in a second axial cross-section perpendicular to the first one, this point becomes the highest point. The saddle 2 is fastened firmly to a tube 3, which forms the upper part of the member 1 and extends downwards as the tube 3', which is engaged slidably inside a tube 11 forming the middle part of the member 1. A screw 10 can be used for adjusting the length of 3' engaged inside 11. An attachment device 4 is integral with the tube 3; it comprises two straps, the ends 5, 6 of which are flexible and, when strapped around the leg, grip each other as can be seen in FIG. 2. An important function of this attachment device will be described later.

An attachment device 14 is provided on tube 11 and it comprises a pair of side straps 15 and 16, similar to 5 and 6. This attachment device 14 can slide on tube 11 in the direction of the longitudinal axis 7, between two adjustable stops 20. It can also rotate by a certain angle as shown in phantom in FIG. 1—around an axis 17 perpendicular to axis 7.

The lower part of member 1 is formed as a tubular leg 12 engaged telescopically inside tube 11 to constitute a rigid assembly of an adjustable length.

A rubber cap 12' ensures the contact with the ground; its resiliency cushions the impacts against the ground, when the apparatus of the invention is used for walking, as will be explained later. The saddle 2 can also be covered with a more or less elastic material or it can be made out of a material which is somewhat flexible.

The lower end of leg 12 is offset backwards with respect to axis 7 (as shown at 13) to function as the user's heel see FIG. 2).

In order to improve the maintaining of the device in place, it can optionally be complemented by a belt 8 passed over the shoulder opposite the leg which is handicapped (FIG 2) and attached by its two front and back ends to saddle 2.

In the second embodiment (FIGS. 3 and 4), the attachment devices are slightly different from those of FIG. 1 and a foot support is provided for the handicapped leg, which consists of a plantar support 21 attached sideways to tube 12. Advantageously, this support can swing slightly, as indicated by the arrow of FIG. 3, so that it may automatically assume the right position for the foot it is meant to support; its vertical position along leg 13 can also be adjusted, for example by using the arrangement shown at the bottom of FIG. 4. A fixed stirrup 22 is placed at the front of the plantar support. At each step, when the user lifts his foot, the top of his foot lifts the plantar support 21 through the stirrup 22 and hence, the whole device is lifted, without any strap being needed.

Instead of stirrup 22, one can also consider the use of two flexible straps similar to 5 and 6 of FIG. 1, which can grip each other to hold the foot. Taking into account the plantar support, the user's handicapped leg is held at three points 4, 14 and 22; it is possible to force the leg to assume a bent position.

In FIGS. 3 and 4, the saddle 2 forming with the first attachment device 4 a single body 24, which is moulded from a plastic which is rigid or semirigid and partly flexible.

The means for holding together the tubes engaged telescopically . are of the type conventionally used in rehabilitation devices, such as for example screws with a head that can be rotated by hand or pins which are snapped into a housing and which can be inserted or removed only through the application of a determined force.

In some cases, it can be advantageous for the user to choose a device for leaning against the ground, the operational length of which he can readily change. For example, lengths which are slightly different depending on whether the user walks or is standing are provided and they can be selected, for example, by operating a lever acting on an eccentric.

It can also be advantageous that the contact of the foot 12, 13 with the ground take place not at the inner side of the heel, but at its outer side, as illustrated in FIG. 5.

The embodiment of FIG. 3 is complemented with a lamp. This lamp 25 produces a light beam pointed in the walking direction. The lamp 25 is fastened by a strap to the tube 11, with an articulation 27 located between the strap and the lamp and allowing an easy adjustment of the direction of the light beam. If desired, the lamp 25 can also be located in the position indicated at 25' in FIG. 3—i.e. fastened to the attachment device 4—or even in the position 25''.

Figure 6:
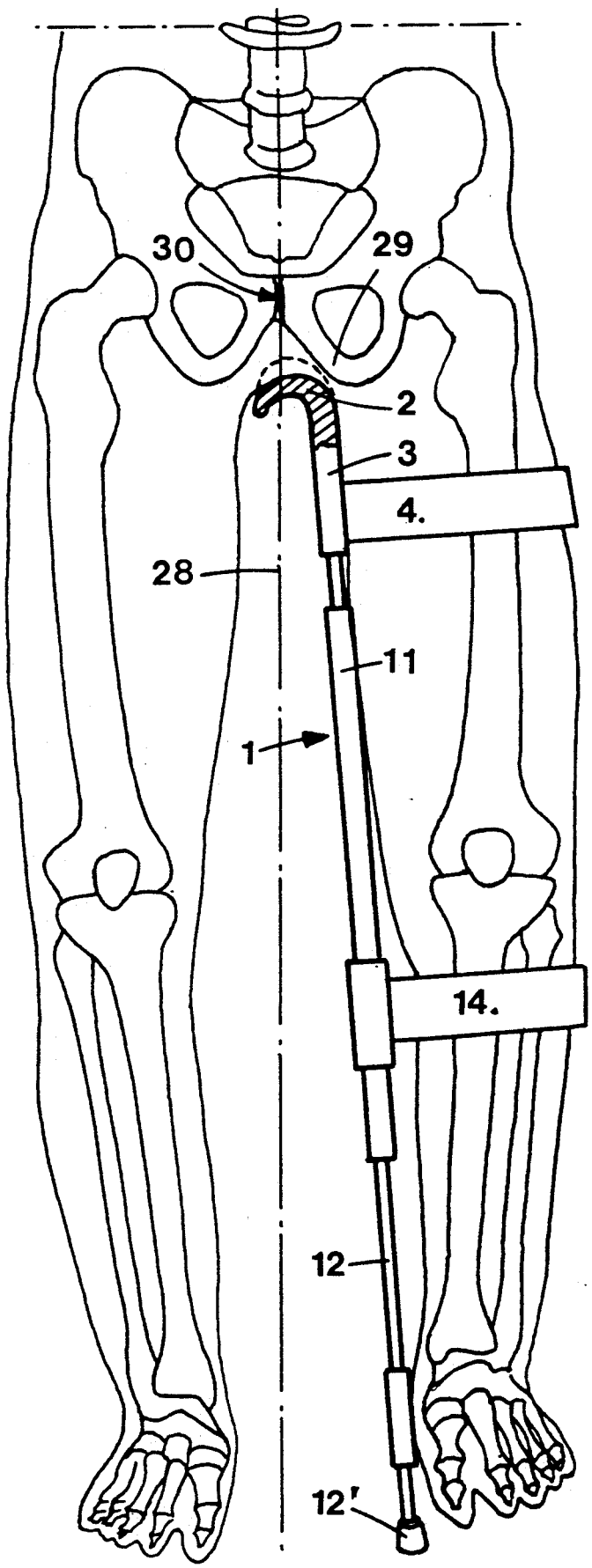
FIG. 6 is a front view showing how the weight of the body acts upon the saddle of the apparatus.

We shall now explain the operations of the apparatuses described above. The active part of the saddle 2 has a width which is notably less than the user's crotch at his groin (see FIGS. 4 and 6). The attachment device 4 has for main function to set the upper region (i.e. 3 and 11) of member 1 against the inside of the thigh of the handicapped leg, as can be seen in FIG. 6. Accordingly, the active surface (i.e. the one which is to receive the weight of the body) of saddle 2 is maintained offset with respect to the medial plane 28 of the user's body, while facing the ischium 29 on the side of the handicapped leg. Thus, when 12' leans against the ground, the weight of the body is transmitted to saddle 2 through the ischium 29. Thus, one avoids applying too much pressure on the symphysis pubis 30, which is fragile, particularly with pregnant women, and unable to withstand high pressures.

Device 4 has another important function, which is to force the apparatus to follow the swinging movements which the user imparts to his handicapped leg, when the other leg, on its own, momentarily supports the total weight of the body. This swinging movement requires a minimal force and the user can, to make it easier, move his foot slightly outwards during these swinging movements.

Of course, the presence of the second attachment device 14 facilitates the swinging movement of the handicapped leg with the apparatus described. However, in the case of a patient whose handicapped leg was amputated, the second attachment device 14 is of no use and the upper attachment device 4 is sufficient to impart to the remaining upper part of the leg and to the apparatus a front-to-back swinging movement, provided the remaining part of the leg measures at least approximately 20 cm.

This is particularly important and advantageous in the case of patients who have just been amputated and who cannot bear wearing an artificial limb, because of the high sensitivity of the stump, during the first year or even several years after the amputation. The apparatus described overcomes this grave problem and can be used as soon as the patient can leave the hospital bed.

One will understand that since a swinging movement can be imparted to the apparatus, the user can walk without using his hands, English canes or any other orthopedic means. He can walk with his hands and his arms completely free and without any other help except the apparatus described here. As he walks, the weight of the body is supported alternately by the healthy leg and by the apparatus; the handicapped leg is never subjected to even a partial load.

Very rapidly, the user can walk in a nearly normal way and the fact that his hands are free helps him at the beginning to maintain his equilibrium; later, he can even carry items such as an umbrella.

Depending on the length given to the apparatus, the sole of the foot may help to walk, which is very useful for maintaining the handicapped limb functioning, for avoiding muscular atrophy of the leg and for facilitating and speeding up rehabilitation.

When the user's foot or his knee need to be treated with particular care and/or if his leg need not be kept straight, the apparatus can be attached to the leg at three locations : by the two attachment devices 4 and 14 and by the plantar support 21 mounted at the desired height on tube 12, 13.

The apparatus described also has the advantage that it allows the user to remain standing for a prolonged period of time, while being supported to a large extent by the apparatus and to a lesser extent by the healthy leg.

We claim:

1. An orthopedic apparatus for person handicapped in one leg, comprising a rigid member (1) having upper and lower portions, first and second ends and an elongated shape, the first end associated with the upper portion and including a saddle (2) for supporting the user's weight, the second end associated with the lower end (12') and including means for leaning against the ground, the saddle (2) having a front portion, a central portion, a back portion and two side portions, wherein the front and back portions are raised with respect to the central portion and the central portion is higher than the side portions to provide a useful surface area which is configured and dimensioned to be engaged between the user's legs, wherein the rigid member (1) is attached to one of the side portions of the saddle and is provided with at least one device (4) for attachment to the handicapped leg, said device operatively associated with the surface area of the saddle and the rigid member for placing the upper portion (3,3') of said rigid member against the inside of the thigh of the handicapped leg while maintaining the useful surface area of the saddle offset with respect to the longitudinal medial plane (28) of the user's body and facing the ischium (29) which is adjacent the handicapped leg, said attachment device (4) including means for allowing the rigid member (1) to follow any swinging movement of the handicapped leg imparted by the user when his other leg supports the whole weight of the user's body, thus making it possible for the user to walk with his hands and arms free and without help from other orthopedic means, wherein the lower end of the rigid member is provided with a plantar support (21), the height and inclination of which can be adjusted, and which is provided with attachment means (22) for forming a stirrup that enables the user to lift the apparatus when lifting the handicapped leg.

2. An apparatus according to claim 1, characterized in that the apparatus further comprises a second device (14) for attachment to the leg in the region comprised between the ankle and the knee, and which can be orientated with respect to the device (1) for leaning against the ground.

3. An apparatus according to claim 1 or 2 characterized in that the lower portion (13) of the member (1) for leaning against the ground is conformed so that the part designed for contacting the ground (12') is located on the outer side of the user's foot (FIG. 5).

4. An apparatus according to claim 1 or 2, characterized in that the lower part (13) of the member 11) is conformed so as to lean against the ground behind the straight line along Which the other part of the member (1) extends.

5. An apparatus according to claim 1 or 2, characterized in that the apparatus further comprises a belt (FIG. 2), the ends of which are fastened to the front end and to the back end of the saddle (2) and which is passed over the user's shoulder opposite the handicapped leg.

6. An apparatus according to claim 1 or 2, characterized in that the apparatus further comprises a lamp fastened thereto in such a manner as to allow an adjustment of the direction of the beam on the ground in front of the user.

7. An apparatus according to claim 1 or 2, characterized in that the length of the rigid member (1) is adjustable.

* * * * *